(12) United States Patent
Su et al.

(10) Patent No.: US 11,135,185 B2
(45) Date of Patent: Oct. 5, 2021

(54) USES OF CURCUMIN DERIVATIVE

(71) Applicant: Merry Life Biomedical Company, Ltd., Tainan (TW)

(72) Inventors: Ih-Jen Su, Tainan (TW); Kuen-Jer Tsai, Tainan (TW); Hong-Yi Chang, Tainan (TW)

(73) Assignee: Merry Life Biomedical Company, Ltd., Tainan (TW)

( * ) Notice: Subject to any disclaimer, the term of this patent is extended or adjusted under 35 U.S.C. 154(b) by 0 days.

(21) Appl. No.: 16/299,511

(22) Filed: Mar. 12, 2019

(65) Prior Publication Data

US 2019/0290604 A1 Sep. 26, 2019

Related U.S. Application Data

(60) Provisional application No. 62/647,501, filed on Mar. 23, 2018.

(51) Int. Cl.
  *A61K 31/165* (2006.01)
  *G01N 33/68* (2006.01)

(52) U.S. Cl.
  CPC ....... *A61K 31/165* (2013.01); *G01N 33/6896* (2013.01); *G01N 2333/775* (2013.01)

(58) Field of Classification Search
  CPC ........... A61K 31/165; G01N 2333/775; G01N 33/6896; A61P 25/28
  See application file for complete search history.

(56) References Cited

U.S. PATENT DOCUMENTS

| | | | |
|---|---|---|---|
| 2008/0188557 A1 | 8/2008 | Shih et al. | |
| 2010/0048901 A1 | 2/2010 | Takahashi et al. | |
| 2011/0112190 A1 | 5/2011 | Chaniyilparampu et al. | |
| 2013/0261121 A1 | 10/2013 | Shih et al. | |
| 2013/0338160 A1* | 12/2013 | Shih | C07C 69/618 514/237.5 |
| 2016/0264539 A1 | 9/2016 | Shih et al. | |
| 2019/0290604 A1 | 9/2019 | Su et al. | |
| 2020/0214997 A1 | 7/2020 | Chan | |

FOREIGN PATENT DOCUMENTS

| | | |
|---|---|---|
| CN | 101558038 A | 10/2009 |
| CN | 101711231 A | 5/2010 |
| CN | 102131765 A | 7/2011 |
| CN | 102225919 A | 10/2011 |
| CN | 104974038 A | 10/2015 |
| CN | 106220507 A | 12/2016 |
| CN | 111407749 A | 7/2020 |
| EP | 3 150 203 A1 | 4/2017 |
| JP | 2014-55134 A | 3/2014 |
| JP | 2014-105196 A | 6/2014 |
| JP | 2015-520233 A | 7/2015 |
| WO | WO 2008/085984 A | 7/2008 |
| WO | WO 2013/192091 A1 | 12/2013 |

OTHER PUBLICATIONS

Heneka et al., Current Neuropharmacology, 2011, 9, 643-650. (Year: 2011).*
Office Action issued in counterpart British Application No. GB1903361.2 dated Jul. 23, 2019 (eight (8) pages).
Office Action issued in counterpart Australian Application No. 2019201665 dated Jun. 26, 2019 (seven (7) pages).
Potter, "Curcumin: a natural substance with potential efficacy in Alzheimer's disease," Journal of Experimental Pharmacology, 2013, pp. 23-31, vol. 5 (nine (9) pages).
Khumsupan et al., "Apolipoprotein E LDL receptor-binding domain-containing high-density lipoprotein: A nanovehicle to transport curcumin, an antioxidant and anti-amyloid bioflavonoid," Biochimica et Biophysica Acta, 2011, pp. 352-359, vol. 1808 (eight (8) pages).
Ray et al., "Neuroinflammation in Alzheimer's disease: different molecular targets and potential therapeutic agents including curcumin," Current Opinion in Pharmacology, 2009, pp. 434-444, vol. 9 (nine (9) pages).
Hamaguchi et al., "Curcumin and Alzheimer's Disease," CNS Neuroscience & Therapeutics, 2010, pp. 285-297, vol. 16 (13 pages).
Villaflores et al., "Curcuminoids and resveratrol as anti-Alzheimer agents," Taiwanese Journal of Obstetrics & Gynecology, 2012, pp. 515-525, vol. 51 (11 pages).
Japanese-language Office Action issued in Japanese Application No. 2019-044362 dated Feb. 18, 2020 with partial English translation (five (5) pages).
Taiwanese-language Office Action issued in Taiwanese Application No. 108108193 dated Apr. 9, 2020 with partial English translation (four (4) pages).
French-language Office Action issued in French Application No. FR1902500 dated Apr. 1, 2020 with partial English translation (nine (9) pages).
Endo et al., "Structure Activity Relationship Study Of Curcumin Analogues Toward The Amyloid-Beta Aggregation Inhibitor", Bioorganic & Medicinal Chemistry Letters, 2014, pp. 5621-5626, vol. 24 (six (6) pages).
Hatcher et al., "Curcumin: from ancient medicine to current clinical trials," Cell Mol Life Sci 2008, 65(11):1631-1652.
Aggarwal et al. "Potential therapeutic effects of curcumin, the anti-inflammatory agent, against neurodegenerative, cardiovascular, pulmonary, metabolic, autoimmune and neoplastic diseases," Int J Biochem Cell Biol 2009, 41(1):40-59.
Darvesh et al., "Curcumin and liver cancer: a review," Curr Pharm Biotechnol 2012, 13(1):218-228.
Jagtap et al., "Chemoprotective mechanism of the natural compounds, epigallocatechin-3-O-gallate, quercetin and curcumin against cancer and cardiovascular diseases," Curr Med Chem 2009, 16(12):1451-1462.

(Continued)

*Primary Examiner* — Jean P Cornet
(74) *Attorney, Agent, or Firm* — Crowell & Moring LLP

(57) ABSTRACT

The invention provides a method for preventing and/or treating Alzheimer's disease in a subject in need of such treatment, comprising administrating to said subject an effective amount of a curcumin derivative, TML-6, and optionally a pharmaceutically acceptable carrier or excipient.

4 Claims, 6 Drawing Sheets
(2 of 6 Drawing Sheet(s) Filed in Color)
Specification includes a Sequence Listing.

(56) References Cited

OTHER PUBLICATIONS

Iappat et al., "Curcumin and obesity: evidence and mechanisms," Nutr Rev 2010, 68(12):729-738.
El-Agamy, "Comparative effects of curcumin and resveratrol on aflatoxin B(1)-induced liver injury in rats," Arch Toxicol 2010, 84(5):389-396.
Chandran et al., "A randomized, pilot study to assess the efficacy and safety of curcumin in patients with active rheumatoid arthritis," Phytother Res 2012, 26(11):1719-1725.
Pallauf et al., "Autophagy, polyphenols and healthy ageing," Ageing Res Rev 2013, 12(1):237-252.
Taylor et al., "Curcumin for inflammatory bowel disease: a review of human studies," Altern Med Rev 2011, 16(2):152-156, 22.
Jager et al., "Comparative absorption of curcumin formulations," Nutr J 2014, 13:11.
Ijaopo, "Dementia-related agitation: a review of non-pharmacological interventions and analysis of risks and benefits of pharmacotherapy," Translational psychiatry 2017, 7(10):e1250.
Alzheimer's Association: "2015 Alzheimer's disease facts and figures," Alzheimer's & dementia: the journal of the Alzheimer's Association 2015, 11(3):332-384.
Lorenzo et al., "Beta-amyloid neurotoxicity requires fibril formation and is inhibited by Congo red," Proc Natl Acad Sci U S A 1994, 91(25):12243-12247.
Dickson, "Apoptotic mechanisms in Alzheimer neurofibrillary degeneration: cause or effect?" J Clin Invest 2004, 114(1):23-27.
Wildsmith et al., "Evidence for impaired amyloid beta clearance in Alzheimer's disease," Alzheimers Res Ther 2013, 5(4):33.
Hesse et al., "Measurement of apolipoprotein E (apoE) in cerebrospinal fluid," Neurochem Res 2000, 25(4):511-517.
Gupta et al., "Plasma apolipoprotein E and Alzheimer disease risk: the AIBL study of aging," Neurology 2011, 76(12):1091-1098.
Banning et al., "Apolipoprotein E and affective symptoms in mild cognitive impairment and Alzheimer's disease dementia: A systematic review and meta-analysis," Neurosci Biobehav Rev. 2019 96:302-315.
Shehzad et al., "Curcumin in inflammatory diseases," Biofactors 2013, 39(1):69-77.
Kumar et al., "Secretase inhibitors for the treatment of Alzheimer's disease: Long road ahead," Eur J Med Chem. Mar. 25, 2018;148:436-452.
Van Dyck, "Anti-Amyloid-β Monoclonal Antibodies for Alzheimer's Disease": Pitfalls and Promise. Biol Psychiatry. 2018 15;83(4):311-319.
Liu et al., "Apolipoprotein E and Alzheimer disease: risk, mechanisms and therapy," Nat Rev Neurol 2013, 9(2):106-118.
De Knijff et al., "Apolipoprotein epsilon 4 and coronary artery disease," Lancet 1992, 340(8831):1351.
Wakuda et al., "Is hyperuricemia a risk factor for arteriosclerosis? Uric acid and arteriosclerosis in apolipoprotein e-deficient mice," Biol Pharm Bull 2014, 37(12):1866-1871.
Schaefer, "Unraveling hyperlipidemia type III (dysbetalipoproteinemia), slowly," Eur J Hum Genet 2009, 17(5):541-542.
Jiang et al., "Effects of ApoE on intracellular calcium levels and apoptosis of neurons after mechanical injury," Neuroscience 2015, 301:375-383.
Braesch-Andersen et al., "ApoE production in human monocytes and its regulation by inflammatory cytokines," PLoS One 2013, 8(11):e79908.
Lee et al., "Tannerella forsythia BspA increases the risk factors for atherosclerosis in ApoE (−/−) mice," Oral Dis 2014, 20(8):803-808.
Cramer et al., "ApoE-directed therapeutics rapidly clear beta-amyloid and reverse deficits in AD mouse models," Science 2012, 335(6075):1503-1506.
Shen et al., "How does curcumin work with poor bioavailability? Clues from experimental and theoretical studies," Sci Rep 2016, 6:20872.
Oddo et al., "Triple-transgenic model of Alzheimer's disease with plaques and tangles: intracellular Abeta and synaptic dysfunction," Neuron 2003, 39(3):409-421.
Canadian Office Action issued in Canadian Application No. 3,036,444 dated Apr. 9, 2020 (four (4) pages).
French-language Office Action issued in French Application No. 1902500 dated Jul. 18, 2019 with English translation (four (4) pages).
Lu, X. et al., "Curcumin suppresses ApoE expression in murine neuroblastoma Neuro2a/APP695 cells", J Third Mil Med Univ, Jan. 15, 2014, pp. 46-49, vol. 36, No. 1, with English abstract (5 pages).
Shie, F-S. et al., "Synergistic effects of an innovative combination therapy on treating Alzheimer's disease involving modulation of gut dysbiosis", Alzheimer's & Dementia, The Journal of the Alzheimer's Association, 2020, (1 page).
Su, I-J. et al., "A Curcumin Analog Exhibits Multiple Biologic Effects on the Pathogenesis of Alzheimer's Disease and improves Behavior, Inflammation, and β-Amyloid Accumulation in a Mouse Model", International Journal of Molecular Sciences, 2020, pp. 1-20, vol. 21, No. 15, 5459. (20 pages).
Ryan, L "Update on Alzheimer's Disease Clinical Trials", Medicines in Development for Alzheimer's Disease, 2010, pp. 1-68.
Miller B. W., et al., "Rosiglitazone and Pioglitazone for the Treatment of Alzheimer's Disease", The Annals of Pharmacotherapy, Nov. 2011, pp. 1416-1424, vol. 45. (9 pages).
Alzheimer's Drug Discovery Foundation, 2018 Alzheimer's Clinical Trials Report, 2018, pp. 1-24. (24 pages).
Hara Y, et al. "Translating the biology of aging into novel therapeutics for Alzheimer disease", Wolters Kluwer Health, Inc. on behalf of the American Academy of Neurology, 2018, pp. 84-94. (11 pages).
Chinese-language Office Action issued in Chinese Application No. 20190197950.0 dated Mar. 1, 2021 with partial English translation (11 pages).
Great Britain Examination Report issued in Great Britain Application No. 1903361.2 dated Apr. 9, 2021 (three (3) pages).
Japanese-language Office Action issued in Japanese Application No. 2019-044362 dated Sep. 29, 2020 with partial English translation (four (4) pages).

\* cited by examiner

SEQUENCE LISTING

<160> NUMBER OF SEQ ID NOS: 18

<210> SEQ ID NO 1
<211> LENGTH: 26
<212> TYPE: DNA

<213> ORGANISM: Artificial Sequence
<220> FEATURE:
<223> OTHER INFORMATION: primer

<400> SEQUENCE: 1
attggtaccg agcaaaggaa cttgat                    26

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
tgagccgaga tctcgccact gca                       23

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3
tgcagtggcg agatctcggc tca                       23

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
atcgaagctt ccggctcctg gggaagga                  28

<210> SEQ ID NO 5
<211> LENGTH: 29
<212> TYPE: DNA
<213> ORGANISM: Artificial Sequence
<220> FEATURE:
<223> OTHER INFORMATION: primer

<400> SEQUENCE: 5
attggtaccg acagtctccc tcttgctga                 29

<210> SEQ ID NO 6
<211> LENGTH: 29
<212> TYPE: DNA
<213> ORGANISM: Artificial Sequence
<220> FEATURE:
<223> OTHER INFORMATION: primer -continued

```
<400> SEQUENCE: 6
attggtacct acaggcgtga gctaccgcc                                            29

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
attggtacca gccccctctc cagattaca                                            29

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
attggtacct ggcccccaga atggaggag                                            29

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
attggtaccc cacctccttc ctccctctg                                            29

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
attggtacca taattggaca agtctggga                                            29

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
ccctgctgtg gggcaggggg ag                                                   22

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12 ctcccccctgc cccacagcag gg                                                  22

<210> SEQ ID NO 13
```

```
<211> LENGTH: 22
<212> TYPE: DNA
<213> ORGANISM: Artificial Sequence
<220> FEATURE:
<223> OTHER INFORMATION: primer

<400> SEQUENCE: 13
ctgtgcctgg ggcaggagaa ca                                                   22

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
tgttctcctg ccccaggcac ag                                                   22

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
gtgactctgg cccagcccgc cctat                                                25

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
atagggcggg ctgggccaga gtcac                                                25

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
tgactggggg ctggcccgcc ctat                                                 24

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
atagggcggg ccagcccca gtca                                                  24
```

USES OF CURCUMIN DERIVATIVE

FIELD OF THE INVENTION

This invention relates to uses of a curcumin derivative. More specifically, the invention relates to uses of a curcumin derivative in preventing and/or treating Alzheimer's disease.

BACKGROUND OF THE INVENTION

*Curcumin* is a major component of *Curcumin longa*, generically known as turmeric, which belongs to the ginger family of perennial plants that grows naturally in India and other parts of Asia. The rhizome of turmeric can be crushed into a yellow powder and then used in Indian delicacies such as curries in Southeast Asia. The major components of turmeric extract are named curcuminoids, which contain about 75% curcumin (diferuloyl methane), 15% demethoxycurcumin, and 10% bisdemethoxycurcumin [Hatcher H, Planalp R, Cho J, Torti F M, Torti S V: *Curcumin: from ancient medicine to current clinical trials. Cell Mol Life Sci* 2008, 65(11): 1631-1652]. Recent studies also indicate that the active ingredient of turmeric is curcumin [Aggarwal B B, Harikumar K B: *Potential therapeutic effects of curcumin, the anti-inflammatory agent, against neurodegenerative, cardiovascular, pulmonary, metabolic, autoimmune and neoplastic diseases. Int J Biochem Cell Biol* 2009, 41(1): 40-59]. Emerging evidence shows that curcumin is effective against a wide variety of diseases like cancer [Darvesh A S, Aggarwal B B, Bishayee A: *Curcumin and liver cancer: a review. Curr Pharm Biotechnol* 2012, 13(1):218-228], cardiovascular disease [Jagtap S, Meganathan K, Wagh V, Winkler J, Hescheler J, Sachinidis A: *Chemoprotective mechanism of the natural compounds, epigallocatechin-3-O-gallate, quercetin and curcumin against cancer and cardiovascular diseases. Curr Med Chem* 2009, 16(12): 1451-1462], obesity [Alappat L, Awad A B: *Curcumin and obesity: evidence and mechanisms. Nutr Rev* 2010, 68(12): 729-738], liver disease [El-Agamy D S: *Comparative effects of curcumin and resveratrol on aflatoxin B*(1)-*induced liver injury in rats. Arch Toxicol* 2010, 84(5):389-396], inflammatory disease [Chandran B, Goel A: *A randomized, pilot study to assess the efficacy and safety of curcumin in patients with active rheumatoid arthritis. Phytother Res* 2012, 26(11):1719-1725] and aging [Pallauf K, Rimbach G: *Autophagy, polyphenols and healthy ageing. Ageing Res Rev* 2013, 12(1):237-252], through multiple molecular targets [Taylor R A, Leonard M C: *Curcumin for inflammatory bowel disease: a review of human studies. Altern Med Rev* 2011, 16(2):152-156, 22; Shehzad A, Rehman G, Lee Y S: *Curcumin in inflammatory diseases. Biofactors* 2013, 39(1): 69-77].

Three major components of turmeric extract, curcumin (diferuloyl methane), demethoxycurcumin, and bisdemethoxycurcumin, are identified and named curcuminoids [Hatcher H, Planalp R, Cho J, Torti F M, Torti S V: *Curcumin: from ancient medicine to current clinical trials. Cell Mol Life Sci* 2008, 65(11):1631-1652]. Although the beneficial effects of curcumin have been suggested by a series of epidemiological investigations, animal experiments, and cell line studies, the low bioavailability and rapid metabolism of curcumin have hindered the therapeutic development of curcumin for human diseases [Jager R, Lowery R P, Calvanese A V, Joy J M, Purpura M, Wilson J M: *Comparative absorption of curcumin formulations. Nutr J* 2014, 13:11].

Alzheimer's disease (AD) is a progressive neurodegenerative disease gaining prevalence worldwide due to increasing lifespan. It has been estimated that the total number of individuals with AD will grow to approximately 74.7 million by 2030 [Ijaopo E O: *Dementia-related agitation: a review of non-pharmacological interventions and analysis of risks and benefits of pharmacotherapy. Translational psychiatry* 2017, 7(10):e1250], and the cost of healthcare will rise to $1 trillion annually by 2050 [Alzheimer's A: 2015 *Alzheimer's disease facts and figures. Alzheimer's & dementia: the journal of the Alzheimer's Association* 2015, 11(3):332-384]. Although more than 100 trials have been conducted in the past decades, few agents are expected to reach market mainly because of inadequate understanding of the complex pathogenesis of AD, and the lack of reliable diagnostic tests or biomarkers to choose the target population. Thus, there is urgent demand for development of therapeutic drugs for AD patients to slow down, arrest, or reverse the progressive decline of cognitive function, especially at the mild cognitive impairment or early stage of AD. The current FDA-approved drugs for AD patients are cholinesterase inhibitor and NMDA antagonist, which act non-specifically and can only alleviate the symptoms with high adverse events.

SUMMARY OF THE INVENTION

The present disclosure demonstrates for the first time that a curcumin derivative, TML-6, can treat and/or prevent Alzheimer's disease by regulating the expression of ApoE through PPARα and RXRα response elements in the APOE promoter.

The present disclosure is to provide a method for preventing and/or treating Alzheimer's disease in a subject in need of such treatment, comprising administrating to said subject an effective amount of TML-6 or a pharmaceutically acceptable salt, solvate, hydrate, isotopologue, or prodrug of TML-6, and optionally a pharmaceutically acceptable carrier or excipient,

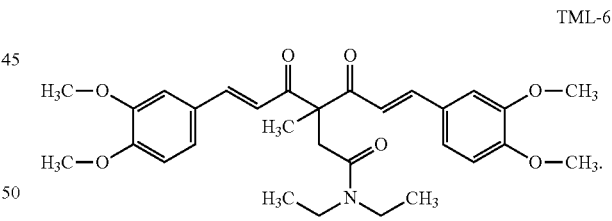

In one embodiment, Alzheimer's disease is treated and/or prevented by regulating apolipoprotein E (ApoE) expression, promoting beta-amyloid (Aβ) clearance, inhibiting amyloid precursor protein (APP) synthesis, and/or inhibiting inflammation in brain regions in a subject in need of such treatment.

The present disclosure also provides a method for identifying a candidate compound which may increase ApoE expression, promote Aβclearance, inhibit APP synthesis, and/or inhibit inflammation in brain regions, which comprises contacting the candidate compound with AP-2 or PPARα/RXRα binding site of ApoE promoter region and determining if the candidate compound binds to AP-2 or PPARα/RXRα binding site of ApoE promoter region, wherein binding indicates that the candidate compound may increase ApoE expression, promote Aβ clearance, inhibit APP synthesis, and/or inhibit inflammation in brain regions.

The present disclosure is described in detail in the following sections. Other characteristics, purposes and advantages of the present invention can be found in the detailed description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
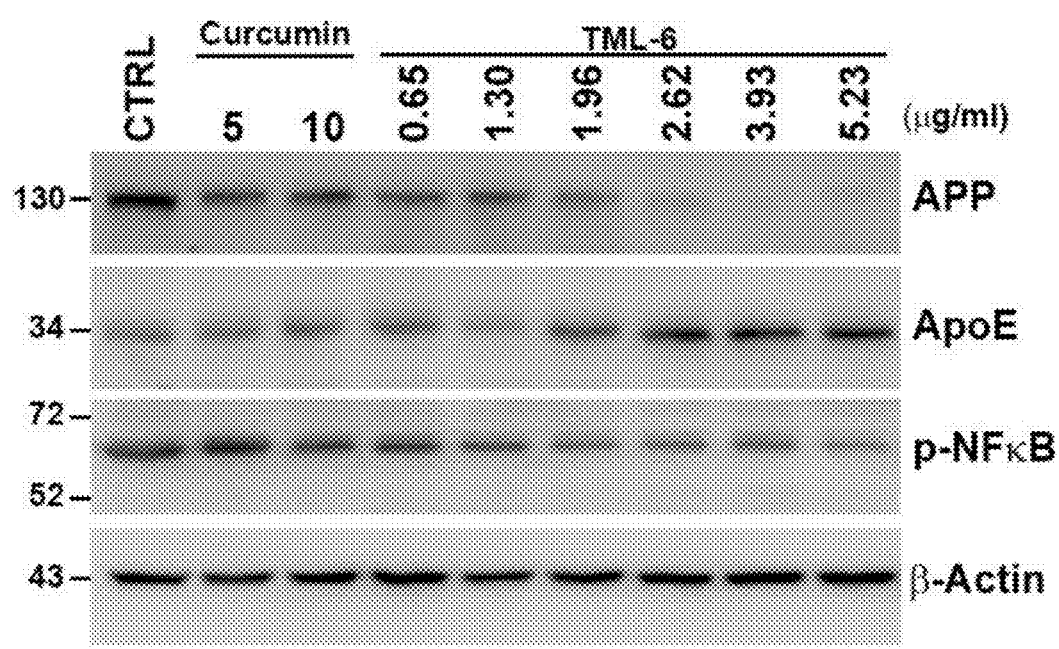
FIG. 1 shows that TML-6 suppresses the expression of APP and phospho-NF-κB and increases the ApoE expression in Huh7 cell line. Huh7 cells were treated with different doses of curcumin and TML-6 for 24 hours. Western blotting was used to examine Alzheimer-related proteins such as APP, ApoE and inflammatory biomarker phosphorylated NFκB.

The present disclosure provides a method for preventing and/or treating Alzheimer's disease in a subject in need of such treatment, comprising administrating to said subject an effective amount of TML-6 or a pharmaceutically acceptable salt, solvate, hydrate, isotopologue, or prodrug of TML-6, and optionally a pharmaceutically acceptable carrier or excipient;

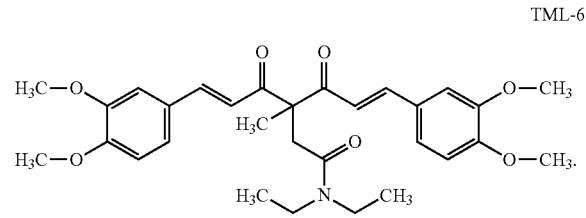 [SMILES: CCN(CC)C(=O)CC(C)(C(=O)/C=C/c1ccc(OC)c(OC)c1)C(=O)/C=C/c1ccc(OC)c(OC)c1]

The present disclosure also provides a method for regulating ApoE expression, promoting Aβ clearance, inhibiting APP synthesis, and/or inhibiting inflammation in brain regions in a subject in need of such treatment, comprising administrating to said subject an effective amount of TML-6, or a pharmaceutically acceptable derivative of TML-6, and optionally a pharmaceutically acceptable carrier or excipient.

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the compounds of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

The term "a pharmaceutically acceptable derivative" or "pharmaceutically acceptable derivatives" as used herein denotes a compound that is modified from the compound of the invention but has properties and efficacies that are the same as or better than those of the compound of the invention. Preferably, the pharmaceutically acceptable derivative is a pharmaceutically acceptable salt, solvate, hydrate, isotopologue, or prodrug of the compound of the invention.

TML-6 of the invention can also exist as a solvate or hydrate. Thus, these compounds may crystallize with, for example, waters of hydration, or one, a number of, or any fraction of molecules of the mother liquor solvent. The solvates and hydrates of such compounds are included within the scope of this invention.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. Examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder, disease or condition to which such term applies, or one or more symptoms of such disorder, disease or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

Alzheimer's disease is a progressive neurodegenerative disease characterized by the presence of two pathological hallmarks: extracellular senile plaques and intracellular neurofibrillary tangles. The senile plaques were found to be composed of β-amyloid in fibrillary aggregation form and can disrupt normal brain function [Lorenzo A, Yankner B A: Beta-amyloid neurotoxicity requires fibril formation and is inhibited by Congo red. *Proc Natl Acad Sci USA* 1994, 91(25):12243-12247]. The intracellular neurofibrillary tangles were later found to be mainly composed of tau protein. Several drugs of cholinesterase inhibitors and NMDA antagonists are available for the treatment of AD patients but the effects are unsatisfactory. These drugs are aiming to improve the symptoms of patients instead of curing the disease.

There are several hypotheses to explain the pathogenesis of AD. The amyloid hypothesis proposes that Aβ accumulates first, and is unable to be removed fast enough by blood flow and so forms insoluble amyloid plaque extracellularly in the process of aging. The Aβ accumulation subsequently triggers tau protein deposition inside the neural cells [Dickson D W: Apoptotic mechanisms in Alzheimer neurofibrillary degeneration: cause or effect? *J Clin Invest* 2004, 114(1):23-27]. Aβ peptide is generated by proteolytic processing from the amyloid precursor protein (APP) through the cleavage by the paired enzyme β-secretase and γ-secretase, leading to production of Aβ40 and Aβ42, which initiate the amyloidogenic process and then aggregate to form the plaque.

Besides Aβ and tau protein, recent studies report that apolipoprotein E (Apo E) also plays a critical role in the catabolism of Aβ clearance. Apo E is the dominant cholesterol and lipid carrier in the brain [Wildsmith K R, Holley M, Savage J C, Skerrett R, Landreth G E: Evidence for impaired amyloid beta clearance in Alzheimer's disease. *Alzheimers Res Ther* 2013, 5(4):33], and dysfunction of Apo E may result in the disruption of Aβ catabolism. In AD patients, the Apo E levels in CSF and plasma tend to be lower than healthy individuals [Hesse C, Larsson H, Fredman P, Minthon L, Andreasen N, Davidsson P, Blennow K: Measurement of apolipoprotein E (apoE) in cerebrospinal fluid. *Neurochem Res* 2000, 25(4):511-517; Gupta V B, Laws S M, Villemagne V L, Ames D, Bush A I, Ellis K A, Lui J K, Masters C, Rowe C C, Szoeke C et al: Plasma apolipoprotein E and Alzheimer disease risk: the AIBL study of aging. *Neurology* 2011, 76(12):1091-1098; Banning L C P, Ramakers I H G B, Deckers K, Verhey F R J, Aalten P: Apolipoprotein E and affective symptoms in mild cognitive impairment and Alzheimer's disease dementia: A systematic review and meta-analysis. Neurosci Biobehav Rev. 2019 96:302-315]. Cramer and colleagues reported that treatment of RXR agonist bexarotene in AD transgenic mouse resulted in enhanced clearance of soluble Aβ within hours and is ApoE-dependent [Cramer P E, Cirrito J R, Wesson D W, Lee C Y, Karlo J C, Zinn A E, Casali B T, Restivo J L, Goebel W D, James M J et al: ApoE-directed therapeutics rapidly clear beta-amyloid and reverse deficits in AD mouse models. Science 2012, 335(6075):1503-1506], suggesting the important role of ApoE in the pathogenesis of AD and potential for development targeting ApoE in AD.

The pathogenesis of AD is further complicated by the inflammation resulting from neural injuries and microglial cell activation, further deteriorating brain function, especially at the late stage of disease. The reduction of inflammation will improve brain function. In the past decade, several drugs targeting a single site such as inhibitors of secretases or antibodies to AP revealed failure, probably due to the complex pathogenesis of AD [Kumar D, Ganeshpurkar A, Kumar D, Modi G, Gupta S K, Singh S K Secretase inhibitors for the treatment of Alzheimer's disease: Long road ahead. Eur J Med Chem. 2018 Mar. 25; 148:436-452; van Dyck C H: Anti-Amyloid-β Monoclonal Antibodies for Alzheimer's Disease: Pitfalls and Promise. Biol Psychiatry. 2018 15; 83(4):311-319.] Therefore, development of drugs targeting multiple pathways of AD pathogenesis will be most desirable in the coming future.

The present disclosure demonstrates that curcumin or its derivative TML-6 can inhibit the APP synthesis, inhibit Aβ synthesis, inhibit NFκB, and upregulate ApoE in vitro. The present disclosure is the first time to demonstrate curcumin derivatives in upregulating ApoE. In an AD transgenic mouse model harboring three mutant genes (APP, Tau, PSEN), the curcumin derivative TML-6 revealed a significantly better activity than curcumin in reducing brain AP level and in inhibiting brain inflammation as assessed by the microglia activation biomarker, Iba-1 expression, testifying to the superior bioavailability of the curcumin derivative TML-6 to traditional curcumin. Therefore, curcumin derivative AML #6 targeting multiple pathways in AD pathogenesis is a therapeutic agent for AD.

Preferably, inhibiting inflammation in brain regions, as assessed by the expression of Iba-1 biomarker is preferably inhibiting inflammation in the brain regions comprise the hippocampus or other frontal regions.

The invention provides a method for preventing and/or treating ApoE-related diseases in a subject in need of such treatment, comprising administrating to said subject an effective amount of TML-6 and optionally a pharmaceutically acceptable carrier or excipient.

Apolipoprotein E is one of the major proteins involved in lipid metabolism in humans and is composed of 299 amino acids. This lipid-binding protein is essential for the catabolic processing of triglyceride-rich lipoproteins. ApoE is produced in the liver and brain and mediates cholesterol metabolism in peripheral tissues. In the central nervous system, ApoE is mainly produced by astrocytes, and transports cholesterol to neurons via ApoE receptors [Liu C C, Liu C C, Kanekiyo T, Xu H, Bu G: Apolipoprotein E and Alzheimer disease: risk, mechanisms and therapy. Nat Rev Neurol 2013, 9(2):106-118]. Therefore, ApoE is known for its biological functions in lipoprotein metabolism and involved in the pathogenesis of cardiovascular diseases. Deficiency of ApoE can result in familial dysbetalipoproteinemia with increased plasma cholesterol and triglycerides due to the impaired clearance of chylomicron, VLDL and LDL remnants [de Knijff P, Jansen H, Lie K I, Havekes L M: Apolipoprotein epsilon 4 and coronary artery disease. Lancet 1992, 340(8831):1351]. Recently, ApoE has been studied in many biological processes not only related to lipoprotein transport but also associated with human diseases such as AD [Wakuda H, Uchida S, Ikeda M, Tabuchi M, Akahoshi Y, Shinozuka K, Yamada S: Is hyperuricemia a risk factor for arteriosclerosis? Uric acid and arteriosclerosis in apolipoprotein e-deficient mice. Biol Pharm Bull 2014, 37(12): 1866-1871; Schaefer J R: Unraveling hyperlipidemia type III (dysbetalipoproteinemia), slowly. Eur J Hum Genet 2009, 17(5):541-542]. ApoE has been associated with increased calcium ion levels and apoptosis following mechanical injury [Jiang L, Zhong J, Dou X, Cheng C, Huang Z, Sun X: Effects of ApoE on intracellular calcium levels and apoptosis of neurons after mechanical injury. Neuroscience 2015, 301:375-383]. Secretion of ApoE by monocytes is downregulated by inflammatory cytokines and upregulated by TGF-β [Braesch-Andersen S, Paulie S, Smedman C, Mia S, Kumagai-Braesch M: ApoE production in human monocytes and its regulation by inflammatory cytokines. PLoS One 2013, 8(11):e79908]. ApoE deficient mice (ApoE−/−) fed high-fat diets showed an acceleration of atherosclerosis in the coronary arteries [Lee H R, Jun H K, Choi B K: Tannerella forsythia BspA increases the risk factors for atherosclerosis in ApoE (−/−) mice. Oral Dis 2014, 20(8):803-808]. Therefore, targeting ApoE may provide therapeutic potential for ApoE-deficiency of human diseases such as atherosclerosis and AD.

ApoE plays a critical role in the catabolism of AO clearance [Wildsmith K R, Holley M, Savage J C, Skerrett R, Landreth G E: Evidence for impaired amyloid beta clearance in Alzheimer's disease. Alzheimers Res Ther 2013, 5(4):33], and dysregulation of ApoE may result in the disruption of Aβ catabolism, leading to the increase of Aβ deposition. Recently, Cramer and colleagues reported that treatment of RXR agonist bexarotene in transgenic mice resulted in enhanced clearance of soluble Aβ with reversal of AD deficit which is ApoE-dependent [Cramer P E, Cirrito J R, Wesson D W, Lee C Y, Karlo J C, Zinn A E, Casali B T, Restivo J L, Goebel W D, James M J et al: ApoE-directed therapeutics rapidly clear beta-amyloid and reverse deficits in AD mouse models. Science 2012, 335(6075):1503-1506]. This result indicates that ApoE is involved in Aβ catabolism and closely related to AD pathogenesis. Therefore, increasing the expression of ApoE in all APOE genotypes may prevent or slow the progression of AD.

The invention demonstrates the upregulation of ApoE by curcumin and TML-6 and further clarifies the transcriptional effect of curcumin and its derivatives on ApoE promoter. The promoter region of ApoE between −154 and +45 contains the critical cis-acting elements of transcriptional factor binding and activation by curcumin, liposomal curcumin and TML-6. According to the prediction of ApoE promoter, we verified PPARα/RXRα and AP2 are the potential response elements in this region. Therefore, curcumin and TML-6 may trans-activate the expression of ApoE through PPARα and RXRα and can potentially provide therapeutic agents for ApoE-related human diseases such as Alzheimer disease.

The invention also provides a method for identifying a candidate compound which may increase ApoE expression, promote Aβclearance, inhibit APP synthesis, and/or inhibit inflammation in brain regions, which comprises contacting the candidate compound with AP-2 or PPARα/RXRα binding site of ApoE promoter region and determining if the candidate compound binds to AP-2 or PPARα/RXRα binding site of ApoE promoter region, wherein binding indicates that the candidate compound which may increase apolipoprotein E expression, promote beta-amyloid clearance, inhibit amyloid precursor protein synthesis, and/or inhibit inflammation in brain regions.

Preferably, the AP-2 binding site of ApoE promoter region is located approximately at positions −120 to −111 and −86 to −76 counting from the transcription start sites.

Preferably, the PPARα/RXRα binding site of ApoE promoter region is located approximately at positions −125 to −114 and −84 to −73 counting from the transcription start site.

In one preferred embodiment of the invention, the method further comprises determining whether the candidate compound enhances expression of a reporter gene operably coupled by ApoE promoter region.

Preferably, the reporter gene includes but is not limited to luciferase.

Preferably, the candidate compounds are a curcumin derivative.

The following examples are provided to aid those skilled in the art in practicing the present invention.

EXAMPLES

Materials and Methods

Cell Culture and Chemicals

The human hepatoma Huh-7 cell lines were obtained from the Health Science Research Resources Bank (JCRB0403; Osaka, Japan) and were cultured in Dulbecco's modified Eagle's medium (DMEM, Gibco) supplemented with 100 U/ml penicillin, 100 mg/ml streptomycin and 10% fetal bovine serum (FBS, Biological industry). Cells were cultured at 37° C. in a humidified atmosphere of 5% $CO_2$ incubator (Forma Scientific, Marietta, Ohio, USA). The cells were seeded in 24-well, 6 or 10 cm dishes overnight the day before the experiment. On the next day, the cells were treated with curcumin (Sigma) and TML-6. The working concentration of each compound is indicated in the figures. The stock concentration was prepared at 5 mg/mL (for curcumin) and 10 mM (for TML-6).

Cell Lysis and Western Blotting

After cells were seeded and treated with curcumin and its derivatives for 24h, cells were washed with ice-cold PBS and lysed with 100 μL of RIPA lysis buffer (Pierce Biotechnology, Rockford, Ill., USA) supplemented with protease and phosphatase inhibitors (Roche Diagnostics, Mannheim, Germany). Cell lysates were further cleaned by centrifugation at 14000 rpm 4° C. for 15 min. Protein concentration was determined using a Bradford assay (Bio-Rad, Hercules, Calif., USA). For western blot analysis, 20 μg of each sample was prepared for SDS-PAGE and denatured at 95° C. for 10 min. The prepared samples from total lysates were loaded and separated by SDS-PAGE (8% or 10%), and then transferred to PVDF membranes (pore size 0.45 μm; PerkinElmer) by semi-dry transfer cell (Bio-Rad). After blocking with 5% Skim milk in PBS-T (0.1% Tween-20), the membranes were hybridized with primary antibodies at 1/1000 dilution at 4° C. overnight. On the next day, membranes were washed with PBS-T followed by incubation with HRP-conjugated anti-mouse or anti-rabbit secondary antibody (DAKO) at 1/5000 dilution at room temperature for 1h as appropriate. Finally, the images were captured by Amersham Imager 600 (GE Healthcare Life Sciences, Marlborough, Mass., USA) after being developed using the chemiluminescent HRP substrate (Millipore). The primary antibodies used in this study were anti-APP, anti-pNFκB (Cell Signaling Technology, Danvers, Mass., USA), anti-ApoE (Abcam, Cambridge, UK), anti-PPARγ, anti-RXRα, and anti-RXRβ (Santa Cruz Biotechnology, Santa Cruz, Calif., USA).

Construction of ApoE promoter, serial deletion and site-directed mutagenesis

The promoter region of human APOE gene has been identified and published [Shen L, Liu C C, An C Y, Ji H F: How does curcumin work with poor bioavailability? Clues from experimental and theoretical studies. *Sci Rep* 2016, 6:20872]. We constructed ApoE promoter region from −1061~+45 in two-steps. The first fragment was amplified using polymerase chain reaction (PCR) by forward primer APOE-F-KpnI: 5'-ATTGGTACCGAGCAAAGGAACTT-GAT-3' (SEQ ID NO: 1) paired with reverse primer APOE-R-BglII: 5'-TGAGCCGAGATCTCGCCACTGCA-3' (SEQ ID NO: 2) and was ligated to the pGL3 basic vector (Promega, Madison, Wis., USA) by using Kpn I and Bgl II restriction sites. The second fragment was amplified using PCR by forward primer APOE-F-BglII: 5'-TGCAGTGGCGAGATCTCGGCTCA-3' (SEQ ID NO: 3) paired with reverse primer APOE-R-HindIII: 5'-ATCGAAGCTTCCGGCTCCTGGGGAAGGA-3' (SEQ ID NO: 4) and was ligated to the pGL3-basic (Promega) by using Bgl II and Hind III restriction sites. The serial deletion mutants of ApoE promoter, −705/+45, −456/+45, −344/+45, −247/+45, −154/+45 and −32/+45 were amplified using PCR and based on the full-length ApoE promoter (−1061/+45). The generated fragments were digested by Kpn I and Xba I and then inserted into the pGL3-basic vector (Promega). To generate the deletion mutants of ApoE promoter, primers were used to amplify the promoter for different lengths. The forward primers were APOE-705-F-KpnI: 5'-ATTGGTACCGACAGTCTCCCTCTTGCTGA-3' (SEQ ID NO: 5), APOE-456-F-KpnI: 5'-ATTGGTACCTA-CAGGCGTGAGCTACCGCC-3' (SEQ ID NO: 6), APOE-344-F-KpnI: 5'-ATTGGTACCAGCCCCCTCTCCAGAT-TACA-3' (SEQ ID NO: 7), APOE-247-F-KpnI: 5'-ATTGGTACCTGGCCCCCAGAATGGAGGAG-3' (SEQ ID NO: 8), APOE-154-F-KpnI: 5'-ATTGGTACCC-CACCTCCTTCCTCCCTCTG-3' (SEQ ID NO: 9), and APOE-32-F-KpnI: 5'-ATTGGTACCATAATTGGACA-AGTCTGGGA-3' (SEQ ID NO: 10) which were paired with reverse primer APOE-R-HindIII: 5'-ATCGAAGCTT-CCGGCTCCTGGGGAAGGA-3' (SEQ ID NO: 4) to amplify the target region of the promoter. For disrupting the binding sites of PPAR and/or AP-2 on ApoE promoter, we conducted the point mutation method and the primers paired used were as follows: −154R1delPPAR-F: 5'-CCCTGCTGTGGGGCAGGGGGAG-3' (SEQ ID NO: 11) paired with −154R1delPPAR-R: 5'-CTCCCCCTGCCC-CACAGCAGGG-3' (SEQ ID NO: 12), −154R1delAP2-F: 5'-CTGTGCCTGGGGCAGGAGAACA-3' (SEQ ID NO: 13) paired with −154R1delAP2-R: 5'-TGTTCTCCTG-CCCCAGGCACAG-3' (SEQ ID NO: 14), −154middelAP2-F: 5'-GTGACTCTGGCCCAGCCCGCCCTAT-3' (SEQ ID NO: 15) paired with −154middelAP2-R: 5'-ATAGGGCGGGCTGGGCCAGAGTCAC-3' (SEQ ID NO: 16), −154middelPPAR-F: 5'-TGACTGGGGGCT-GGCCCGCCCTAT-3' (SEQ ID NO: 17) paired with −154middelPPAR-R: 5'-ATAGGGCGGGCCAGCCCCCA-GTCA-3' (SEQ ID NO: 18). The pGL3-154/+45-ApoE-Luc was used as the template for PCR reaction to amplify the mutant of PPAR or AP-2 binding sites in the ApoE promoter. The PCR products were digested by Dpn I and transformed into TOP10 competent cells (Invitrogen, Carlsbad, Calif., USA). After LB plating and extraction of plasmids, positive colonies were confirmed by restriction enzyme digestion. All of the promoter constructs were verified by sequencing.

Luciferase Reporter Assay

The Huh-7 cells were seeded in 24-well culture plates and then co-transfected with serial deletion of pGL3-ApoE-Luc (firefly luciferase) with pRL-TK renilla luciferase reporter. Following overnight incubation, the transfected cells were treated with traditional curcumin, and TML-6 for an additional 24h. The luciferase report assay was done using the Dual-Luciferase Report assay system (Promega). The cell lysates were assayed for both firefly and renilla luciferase activities. The relative luciferase units (RLU) were measured using a luminometer (GLOMAX Multi, Promega). Firefly luciferase activity was normalized for transfection efficiency using the Renilla luciferase activity in each lysate as the control. The RLUs are expressed as means plus standard deviation of three independent experiments.

AD Transgenic Mice and Cell Line

Triple-transgenic mice as a model of Alzheimer's disease (3×Tg-AD, APP Swedish, MAPT P301L, and PSEN1 M146V) were bred at the laboratory animal center of National Cheng Kung University (NCKU) [Oddo S, Caccamo A, Shepherd J D, Murphy M P, Golde T E, Kayed R, Metherate R, Mattson M P, Akbari Y, LaFerla F M: Triple-transgenic model of Alzheimer's disease with plaques and tangles: intracellular Abeta and synaptic dysfunction. *Neuron* 2003, 39(3):409-421]. Experimental procedures for handling the mice were in accordance with the guidelines of the Institutional Animal Care and Use Committee (IACUC) of NCKU. The mice were housed in a room maintained on a 12-h light-dark cycle and fed ad libitum. Sixteen-month-old 3×Tg-AD mice were used in animal experiments. These mice developed plaque and tangle pathology. Aβ deposition as progressive deposition appeared as early as six months.

Immunofluorescence Staining

Mice were anesthetized and euthanized with 10% chloral hydrate (400 mg/kg, i.p.) and then transcardial perfusion was performed with 0.01 M PBS (pH 7.4). The brains were post-fixed in 4% PFA for 2 days and dehydrated with 30% sucrose at 4° C. The hydrated brain was embedded with optimal cutting temperature compound (OCT, Leica) and quick-frozen at −30° C. The blocks were sectioned at 16 um-thick. Slices were stored at −20° C. Before immunofluorescence staining, the sections were soaked in cold PBS for 5 min. Antigen retrieval was performed with 0.01 M citrate acid at 100° C. for 5 min. The sections were then blocked with 5% normal donkey serum (Millipore, Temecula, Calif.) containing 0.1% Triton X-100 (Sigma) in PBST. Primary antibody Iba1 (Wako, 1:400), and Aβ (Covance, 1:100) were used at room temperature for 1 hr. Alexa Fluor 488-conjugated anti-rabbit antibody (for Iba1, Invitrogen Life Technologies, 1:300), Alexa Fluor 594-conjugated anti-mouse antibody (for GFAP, Invitrogen Life Technologies, 1:300) and Alexa Fluor 488-conjugated anti-mouse antibody (for Aβ, Invitrogen Life Technologies, 1:300) were used respectively. The images were captured by TissureFAXS microscopy system and positive signals were quantified by TissueQuest software module (TissueGnostic, Vienne, Austria).

Amyloid β Enzyme-Linked Immunosorbent Assay

Figure 2:
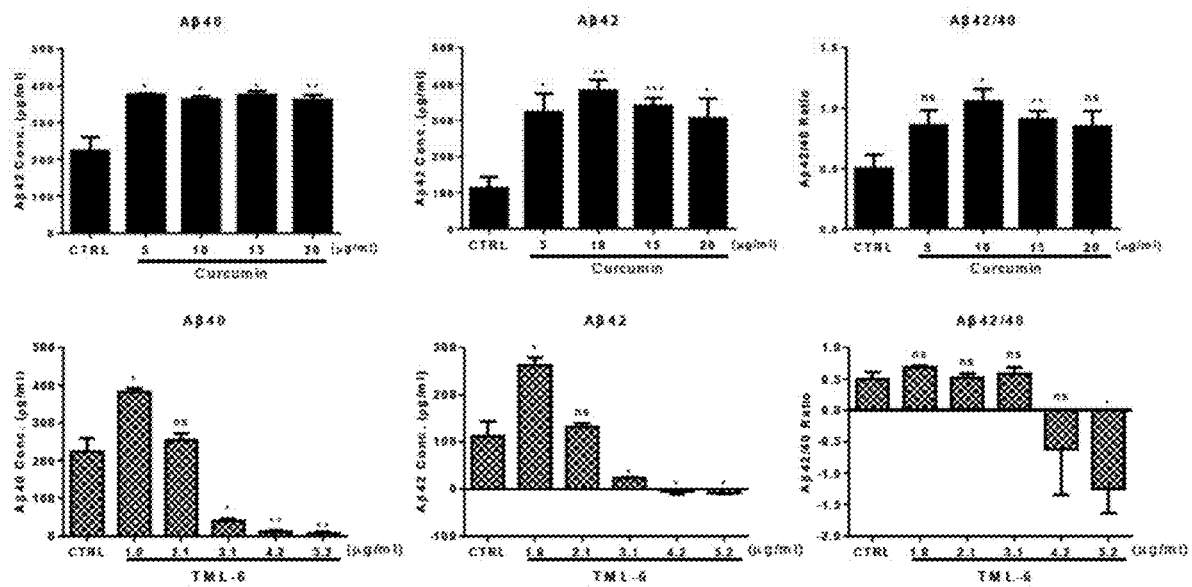
FIG. 2 shows that TML6 suppresses the Aβ production in N2a/APPswe stable cell line. The stable over-expression of APP Swedish mutant in N2A cell line (N2a/APPswe) was treated with different doses of curcumin and TML-6. After 24 h incubation, the levels of Aβ40, Aβ42 and Aβ42/40 ratio in the culture medium were examined by Colorimetric BetaMark Beta-Amyloid x-40 and x-42 ELISA Kit.

Extracellular levels of soluble Aβ40 and Aβ42 were determined by LEGEND MAX™ β-Amyloid x-40 and X-42 ELISA Kit (Biolegend). N2A neuroblastoma cell line with stably over expressing APP Swedish mutation (APPswe) was designed as N2A/APPswe cell line (kindly grafted from Prof. Kuo, Yu-Min's Lab). $8 \times 10^5$ N2A/APPswe cells were seeded on a 6-cm dish. After overnight incubation, the cells were treated with curcumin or TML-6 for 24 h. The working concentrations of curcumin and TML-6 diluted in DMEM medium are as indicated in FIG. 2. The culture supernatant was collected and centrifuged at 1,500×g at 4° C. for 5 min to remove cells. The Aβ levels of the culture supernatants of various treatments were assayed according to the manufacture's instrumentations. The samples were detected at OD620 and the calculation of Aβ levels was based on the standard curves of Aβ40 and Aβ42, respectively.

Statistical Analysis

The significance of different lengths of ApoE promoter by luciferase reporter assay between traditional curcumin and curcumin derivatives (ASC compound), and site-directed mutagenesis on PPAR and AP2 after treatment with curcumin and TML-6 were determined by two-way ANOVA (*$P<0.05$, $P<0.01$, *$P<0.001$, ****$P<0.0001$). The significance of serial deletion mutants of ApoE promoter after treatment with traditional curcumin and ASC compounds and siRNA knockdown experiments were determined by paired t test (*$P<0.05$,$P<0.01$, *$P<0.001$). Data represent the mean with standard deviation (SD) error bar.

Results

To examine the protein expression levels of several critical biomarkers, Huh-7 cells were treated with traditional curcumin and TML-6 for 24h, followed by Western blotting analysis. Our result indicated that protein expression levels of APP and phospho-NF-κB decreased in a dose-dependent manner after treatment with TML-6 for 24 hr. On the other hand, protein expression levels of Apo E significantly increased in TML6 treatment (FIG. 1). Traditional curcumin was used as a positive control in this experiment. These results indicate that TML-6 inhibits inflammatory response by suppressing phosphorylation of NFκB protein. The expression levels of APP are also suppressed by TML-6. On the contrary, protein level of ApoE was increased after treatment with TML-6.

To examine whether Aβ production was affected by TML-6, stable cell line N2a/APPswe was treated with traditional curcumin, TML-6 for 24h incubation. Secreted AP was examined in culture medium by using ELISA. These data show that TML-6 significantly suppresses the production of Aβ40, Aβ42 and Aβ42/40, but not in curcumin (FIG. 2).

Figure 3:
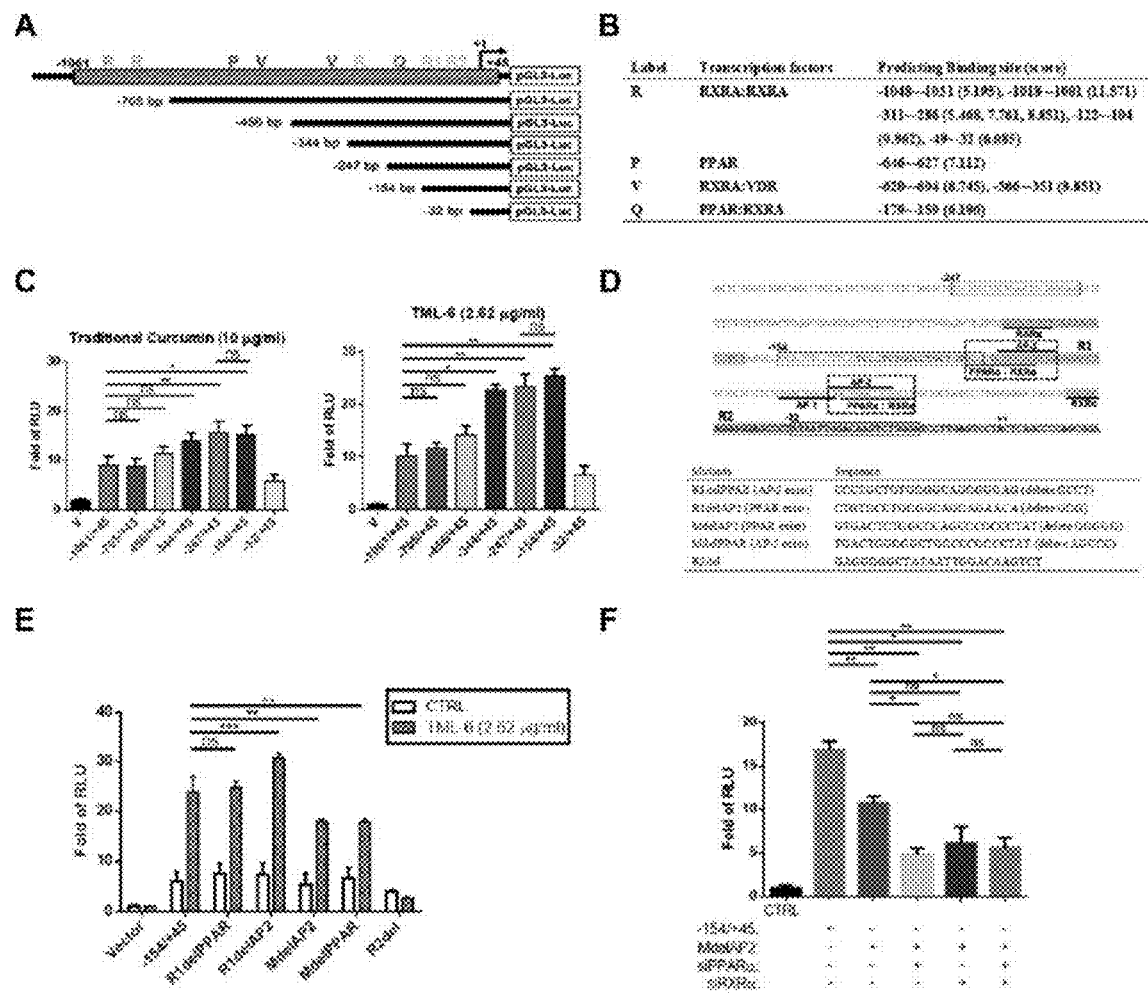
FIG. 3 shows that the promoter activity of ApoE is regulated by TML-6 through the transcriptional regulation of PPARα/RXRα and AP-2 binding site between −154 and +45 on ApoE promoter region. (A) Schematic representation of the potential binding sites on the full-length (−1061/+45) and serial deletion mutants of ApoE promoter constructs. The potential binding sites were predicted by JASPAR database (http://jaspar2016.genereg.net/). (B) The abbreviation of transcription factor binding sites and scores are shown based on prediction results of ApoE promoter. (C) Huh-7 cells were transiently co-transfected with different lengths of ApoE promoter and pRL-TK plasmids. After incubation with traditional curcumin or TML-6, the luciferase reporter activities of the cell lysates were measured. (D) Upper panel shows the putative binding sites of PPARα/RXRα and AP-2 between −154 and +45 on ApoE promoter. AP2 binding sites locate at −120 to −111 and −86 to −76, and PPARα/RXRα binding sites locate at −125 to −114 and −84 to −73 of −154/+45 ApoE promoter region. Two dotted-square boxes show the distal and proximal binding sites of PPARα/RXRα and AP-2 on ApoE promoter, respectively. Lower panel indicates the mutations of PPARα/RXRα and AP-2 binding sites by site-directed mutagenesis. (E) Huh-7 cells were co-transfected with mutants of ApoE promoter and pRL-TK plasmids. After incubation with TML-6 for 24h, the luciferase reporter activities of the cell lysates were measured. (F) The mutant form of ApoE promoter (−154/+45MdelAP2) was co-transfected with siPPARα and/or siRXRα into Huh7 cells. After incubation with TML-6 for 24h, the luciferase reporter activities of the cell lysates were measured. The results are presented as folds of RLU after normalization using renilla luciferase activity. The means±SD are derived from three independent experiments. *P<0.05; P<0.01; *P<0.001; NS: not significant (paired t-test).

The full-length (−1061/+45) and serial deletions of ApoE promoter were shown in FIG. 3A. The transcriptional binding sites on ApoE promoter were predicted by JASPAR open-access database (http://jaspar2016.genereg.net/). Based on the prediction, we constructed serial deletion mutants of the ApoE promoter region between −1061 to +45 into pGL3-basic vector (FIG. 3B) followed by analyzing the promoter activity with a luciferase reporter assay. The luciferase activity of ApoE promoter gradually increases as serial truncations of ApoE promoter region from 5'-end to 3'-end after treatment traditional curcumin and TML-6 (FIG. 3C). These results demonstrate that the region between −154 and +45 on ApoE promoter exist a positive regulatory element for ApoE gene transcriptional activation.

The prediction of transcription factor binding sites of AP-2 were located overlapped with PPARα/RXRα on ApoE promoter between −154 and +45 as shown in FIG. 3D. More specifically, two AP2 binding sites of ApoE promoter region at −120 to −111 and −86 to −76 which overlap two PPARα/RXRα binding sites at −125 to −114 and −84 to −73 are shown in FIG. 3D-upper panel. Therefore, disruption of PPARα/RXRα and AP-2 binding sequences with partial deletion of ApoE promoter between −154 and +45 was carried out by site-directed mutagenesis (FIG. 3D-lower panel). For example, the distal overlapping PPARα/RXRα and AP-2 binding sites were designed through the mutant construct R1delPPAR in which the GCCT motif (partial binding motif of PPARα/RXRα) was deleted and the entire AP2 binding motif was preserved. On the other hand, for the mutant construct of R1 delAP2, the AP2 binding site was partially disrupted and the PPAR binding site was preserved. ApoE promoter activity was significantly suppressed by disruption of the proximal PPARα/RXRα and AP2 binding sites (MdelAP2 and MdelPPAR), which were responsible for ApoE transcriptional activation by TML-6 (FIG. 3E). Therefore, proximal AP2 and PPARα/RXRα binding sites at −86 to −76 (AP-2) and −84 to −73 (PPARα/RXRα) are critical for ApoE transcriptional activation by TML-6.

In order to clarify the role of PPARα on ApoE promoter transcriptional activation by TML-6, we chose the MdelAP2 (proximal AP2 binding site was disrupted) mutated construct of ApoE-154/+45 in a siRNA knockdown experiment to examine the transcriptional regulation of ApoE in response to TML-6. Our data shows that the promoter activity of ApoE-154MdelAP2/+45 mutant was suppressed compared with wild-type ApoE promoter region from −154 to +45 after treatment with TML-6 (FIG. 3F). Moreover, the activities of ApoE promoter are the lowest when PPARα, RXRα and AP2 were knocked down. On this basis, our data indicates that knockdown of PPARα significantly suppresses the effect of AP2 disruption of ApoE promoter (FIG. 3F).

Figure 4:
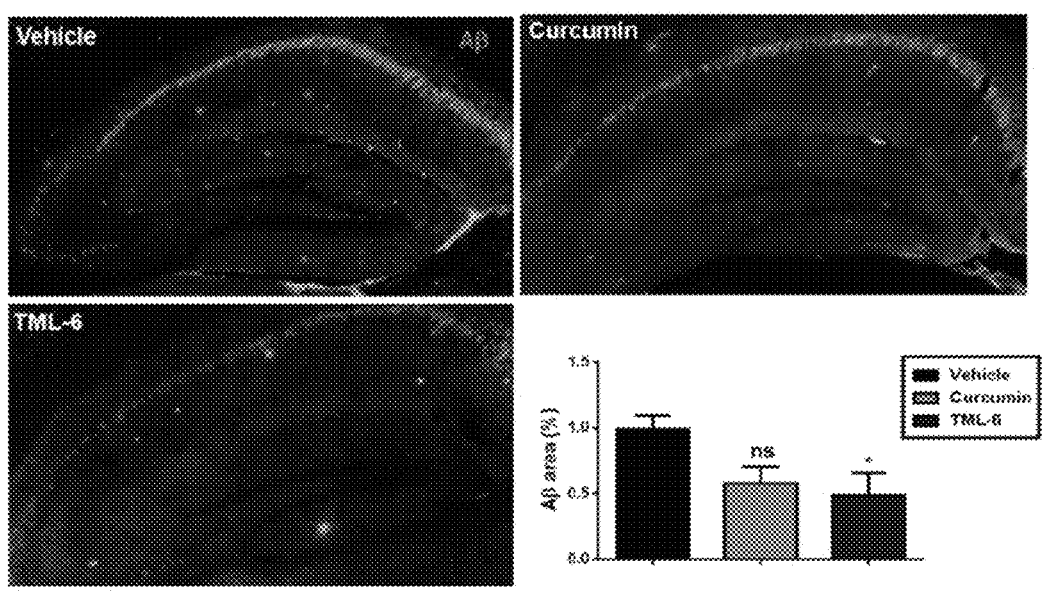
FIG. 4 shows that TML-6 reduces Aβ levels in the brain of triple-gene mutants AD (3×Tg AD) transgenic mice. TML-6 significantly reduces Aβ levels in the brain of 3×Tg AD transgenic mice. Six-month-old 3×Tg-AD mice were fed with curcumin and 150 mg/kg of TML-6 with for four months. The mice brain sections were examined by Aβ immunofluorescence staining.

To examine the efficiency of TML-6 as a therapeutic drug for AD, six-month-old 3×Tg AD transgenic mice were fed with curcumin and its derivative TML-6 for four months at dosage of 150 mg/kg. The Aβ levels significantly decrease in the brain of 3×Tg AD transgenic mice treated with TML-6 as examined by Aβ immunofluorescence staining (FIG. 4).

Figure 5:
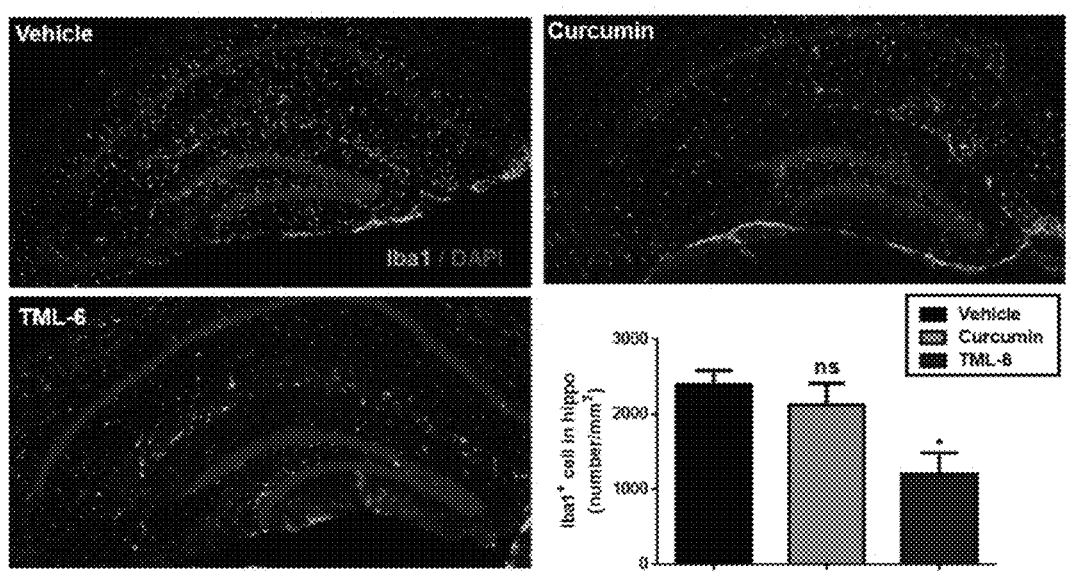
FIG. 5 shows that TML-6 reduces the inflammatory biomarker Iba-1 in 3×Tg AD transgenic mice. *Curcumin* derivative-TML-6 reduces the inflammatory biomarker Iba1 in AD transgenic mice. Six-month-old 3×Tg-AD mice were fed with curcumin and TML-6 (150 mg/kg). After feeding for four months, the inflammatory biomarker of Iba-1 was detected and analyzed by Iba-1 immunofluorescence staining in 3×TgAD transgenic mice.

To examine whether brain inflammation was suppressed by TML-6, we examined the expression of Iba-1, an inflammatory biomarker of microglial activation, after feeding with curcumin and TML-6. The data indicated that TML-6 significantly inhibited the expression of Iba-1 in AD transgenic mice after feeding them with TML-6 as compared to curcumin in triplex AD mice experiments (FIG. 5).

Figure 6:
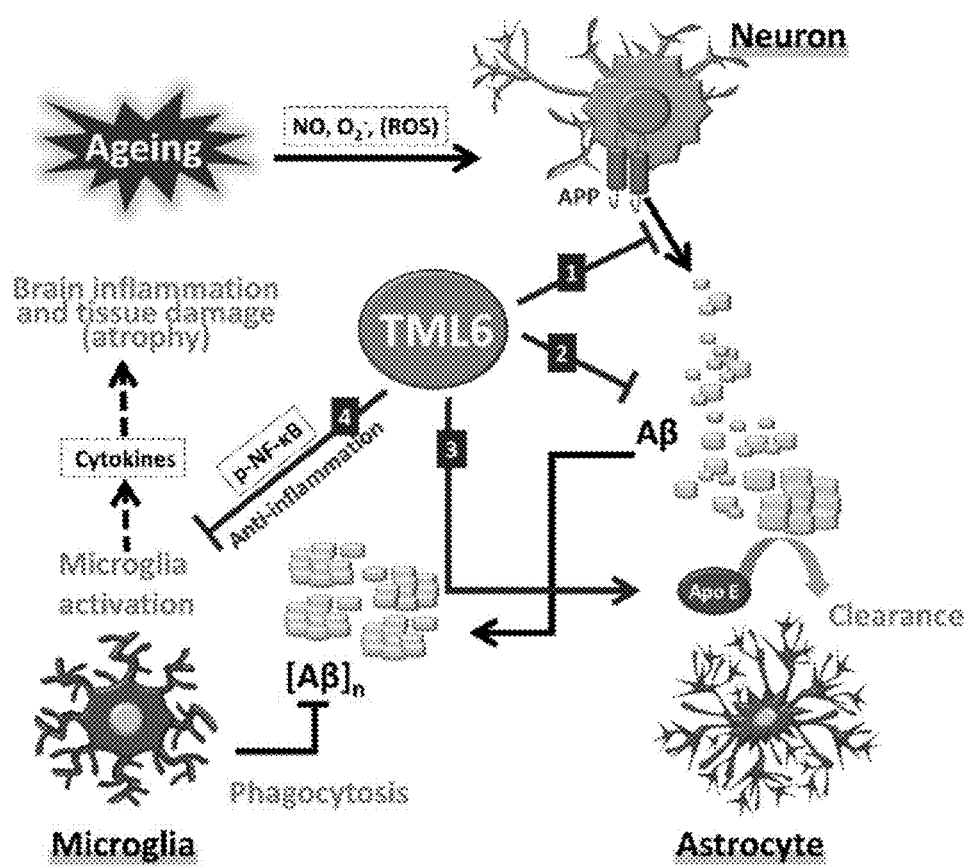
FIG. 6 shows the action mechanism of TML-6 in the therapy of Alzheimer's disease. *Curcumin* derivative-TML-6 treatments can (1) inhibit the production of Aβ from APP; (2) suppress the secretion of Aβ in neuron cells; (3) in astrocyte, activate transcription of APOE and enhance the clearance of Aβ; (4) in the microglia cells, achieving the anti-inflammatory effect by inhibiting the phosphorylation of NF-κB and lowering the inflammation in the AD brain.

Taken together, the action mechanism of TML-6 is proposed and shown in FIG. 6. *Curcumin* derivative-TML-6 treatment can inhibit the synthesis of APP and the production of AP from APP, thereby suppressing the secretion of AP. Therefore, the transcriptional activation of APOE may enhance the clearance of Aβ in astrocytes. In vitro, curcumin and TML-6 have the anti-inflammatory effect achieved by inhibiting phosphorylation of NFκB, which is consistent with the lowering of inflammation in the brain region as assessed by the expression of Iba-1, a microglial activation biomarker (FIG. 5).

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for treating Alzheimer's disease in a subject in need of such treatment, comprising administrating to said subject an effective amount of TML-6, or a pharmaceutically acceptable salt, solvate, hydrate, isotopologue, or prodrug of TML-6, and optionally a pharmaceutically acceptable carrier or excipient,

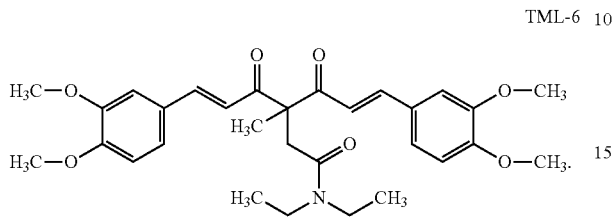

TML-6

2. The method according to claim 1, which is for increasing apolipoprotein E expression, promoting beta-amyloid clearance, inhibiting amyloid precursor protein synthesis, and/or inhibiting inflammation in brain regions.

3. The method according to claim 2, which is for increasing apolipoprotein E expression, promoting beta-amyloid clearance, inhibiting amyloid precursor protein synthesis, and inhibiting inflammation in brain regions.

4. The method according to claim 2, wherein the brain regions comprise hippocampus or other frontal regions.

* * * * *